(12) United States Patent
Murakami et al.

(10) Patent No.: US 10,126,250 B1
(45) Date of Patent: Nov. 13, 2018

(54) FOREIGN SUBSTANCE ANALYSIS SYSTEM

(71) Applicant: Shimadzu Corporation, Kyoto (JP)

(72) Inventors: Sachio Murakami, Kyoto (JP); Shoko Iwasaki, Kyoto (JP); Tsuyoshi Tsuchibuchi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 15/690,950

(22) Filed: Aug. 30, 2017

(51) Int. Cl.
| | |
|---|---|
| *G01J 5/02* | (2006.01) |
| *G01N 21/94* | (2006.01) |
| *G01N 23/207* | (2018.01) |
| *G01N 21/35* | (2014.01) |
| *G01N 21/17* | (2006.01) |

(52) U.S. Cl.
CPC ............. *G01N 21/94* (2013.01); *G01N 21/35* (2013.01); *G01N 23/2076* (2013.01); *G01N 2021/1748* (2013.01); *G01N 2021/3595* (2013.01); *G01N 2201/0636* (2013.01); *G01N 2223/063* (2013.01); *G01N 2223/076* (2013.01); *G01N 2223/652* (2013.01)

(58) Field of Classification Search
CPC .................. G01N 23/20083; G01N 33/12
See application file for complete search history.

(56) References Cited

U.S. PATENT DOCUMENTS 4,122,139 A * 10/1978 Yajima ............... C04B 35/571
264/133
5,428,657 A * 6/1995 Papanicolopoulos ...............
G01N 23/20083
378/86

FOREIGN PATENT DOCUMENTS

| JP | H06-194319 A | 7/1994 |
| JP | 2000-258340 A | 9/2000 |
| JP | 2010-223908 A | 10/2010 |

OTHER PUBLICATIONS

Japanese Office Action dated Aug. 21, 2018, in connection with corresponding JP Application No. 2015-057291 (9 pgs., including English translation).

VD Hodoroaba, et al., "Gaining improved chemical composition by exploitation of Compton-to-Rayleigh intensity ratio in XRF analysis", in Anal Chem, vol. 86, No. 14, Jul. 15, 2014, pp. 6858-6864 (1 pg., only an Abstract provided).

Rie Ogawa, et al., "X-Ray Fluorescence Analysis for Small Quantities of Organic Samples Using Theoretical Intensity of Scattered X-rays", in Progress, Mar. 31, 2011, (X ray technical-analysis 46th collection), pp. 315-324 (30 pgs., including English translation).

* cited by examiner

*Primary Examiner* — Kiho Kim
(74) *Attorney, Agent, or Firm* — Maier & Maier, PLLC

(57) ABSTRACT

A foreign substance analysis system capable of accurately and easily analyzing a foreign substance contained in a sample. The foreign substance analysis system includes an infrared spectrum acquisition step of acquiring infrared spectrum information of a sample measured by an infrared spectrophotometer; and a fluorescent X-ray spectrum acquisition step of acquiring fluorescent X-ray spectrum information of the sample measured by a fluorescent X-ray analyzer; and a determination step of determining whether or not an organic element is contained in the sample by comparing a ratio of an intensity of a Compton scattered ray and an intensity of a Rayleigh scattered ray in the fluorescent X-ray spectrum information with a set threshold value.

6 Claims, 3 Drawing Sheets

FOREIGN SUBSTANCE ANALYSIS SYSTEM

BACKGROUND OF THE INVENTION

Field of the Invention

The present invention relates to a foreign substance analysis system capable of analyzing foreign substance contained in a sample.

Description of the Related Art

In the related art, analysis of foreign substance contained in a sample is required. Therefore, a Fourier transform infrared spectrophotometer (FTIR) is used to analyze organic substances (particularly, film, plastic, rubber, or the like) contained in the sample.

A Michelson two-beam interferometer used as such an FTIR has a configuration where infrared light emitted from an infrared light source is divided by a beam splitter into two direction beams toward a fixed mirror and a movable mirror, infrared light reflected by a fixed mirror and returned and infrared light reflected by the movable mirror and returned are combined by the beam splitter, and the combined infrared light is transmitted to one optical path. At this time, if the movable mirror moves forward and backward in the incident optical axis direction, a difference in the optical path lengths of the two divided light fluxes changes, so that the combined light becomes interference light (interferogram) of which light intensity varies with the position of the movable mirror.

Then, the surface of the sample is irradiated with such interference light, the wavelength of the light reflected on the surface of the sample is acquired by an infrared detector, and organic substances contained in the sample are quantified by referring to a library (for example, refer to JP-A-2002-148116).

On the other hand, in the case of analyzing inorganic substances (for example, Ca, Zn, Si, Al, Mg, S, P, Fe, Cl, Cu, or the like) contained in the sample, a fluorescent X-ray analyzer (EDX), an atomic absorption photometer (AA), or an inductively coupled plasma emission spectrometer (ICP) are used.

For example, in the EDX, the surface of a sample is allowed to emit light by arc discharge or spark discharge, the emitted light is introduced into a spectroscope, a spectrum having a wavelength peculiar to each element is extracted and detected, and component concentration is calculated from the intensity of the obtained spectrum.

With the sample diversification in recent years, with respect to samples containing organic substances and inorganic substances, it has become important to analyze the organic substances and the inorganic substances, and analysts analyze such samples with the EDX together with the FTIR.

However, in the case of analyzing a sample by using the FTIR and the EDX, analysis results may differ depending on the analyst due to the analyst's knowledge, and it may be difficult for an inexperienced analyst to perform the analysis.

SUMMARY OF THE INVENTION

The invention is to provide a foreign substance analysis system capable of accurately and easily analyzing a foreign substance contained in a sample.

According to an aspect of the invention, there is provided a foreign substance analysis system including: an infrared spectrum acquisition step of acquiring infrared spectrum information of a sample measured by an infrared spectrophotometer; and a fluorescent X-ray spectrum acquisition step of acquiring fluorescent X-ray spectrum information the sample measured by a fluorescent X-ray analyzer; and a determination step of determining whether or not an organic element is contained in the sample by comparing a ratio of an intensity of a Compton scattered ray and an intensity of a Rayleigh scattered ray in the fluorescent X-ray spectrum information with a set threshold value.

Herein, the "set threshold value" is an arbitrary numerical value determined in advance by a designer or the like, and is, for example, "1.0".

As described above, according to the foreign substance analysis system according to the invention, it is possible to easily determine whether or not an organic element is contained in a sample.

In addition, in the above aspect of the invention, the foreign substance analysis system may further include: a generation step of generating main component information indicating at least one type of element having a high content on the basis of the fluorescent X-ray spectrum information in assumption that a composition formula of main components of the sample is $CH_2O$ when it is determined that the organic element is included in the determination step; a detection step of detecting N types of elements having high contents on the basis of the infrared spectrum information, the main component information and a library; and a quantification step of using the N types of elements detected in the detection step as main components of the sample and quantifying the elements contained in the sample on the basis of the fluorescent X-ray spectrum information.

The "N types" are arbitrary numerical values determined in advance by designers or the like and are, for example, "three types", "ten types", or the like.

In addition, in the above aspect of the invention, the foreign substance analysis system may further include: a generation step of generating main component information indicating at least one type of element having a high content on the basis of the fluorescent X-ray spectrum information when it is determined that the organic element is not contained in the determination step; a detection step of detecting N types of elements having high contents on the basis of the infrared spectrum information, the main component information, and the library; and a quantification step of using the N types of elements detected in the detection step as the main components of the sample and quantifying the element contained in the sample on the basis of the fluorescent X-ray spectrum information.

According to the foreign substance analysis system according to the invention described above, since the analysis is substantially automated, it possible to realize more-accurate mixed foreign substance analysis in a short time.

In addition, in the above aspect of invention, the foreign substance analysis system may further include: an appearance information acquisition step of acquiring appearance information of the observed sample; and a storage step of storing a dedicated library illustrating a relationship between the appearance information and element information in the infrared spectrum information.

In addition, in the above aspect of the invention, the appearance information may be color, shape, hardness and/or gloss.

In addition, in the above aspect of the invention, in the storage step, a general library indicating the element information in the infrared spectrum information may be stored, and in the detection step, it may be selected whether to use the dedicated library or to use the general library.

DETAILED DESCRIPTION OF THE INVENTION

Hereinafter, embodiments of the invention will be described with reference to the drawings. In addition, the invention is not limited to the embodiments described below, but various embodiments are included within the scope of the invention not departing from the spirit of the invention.

Figure 1:
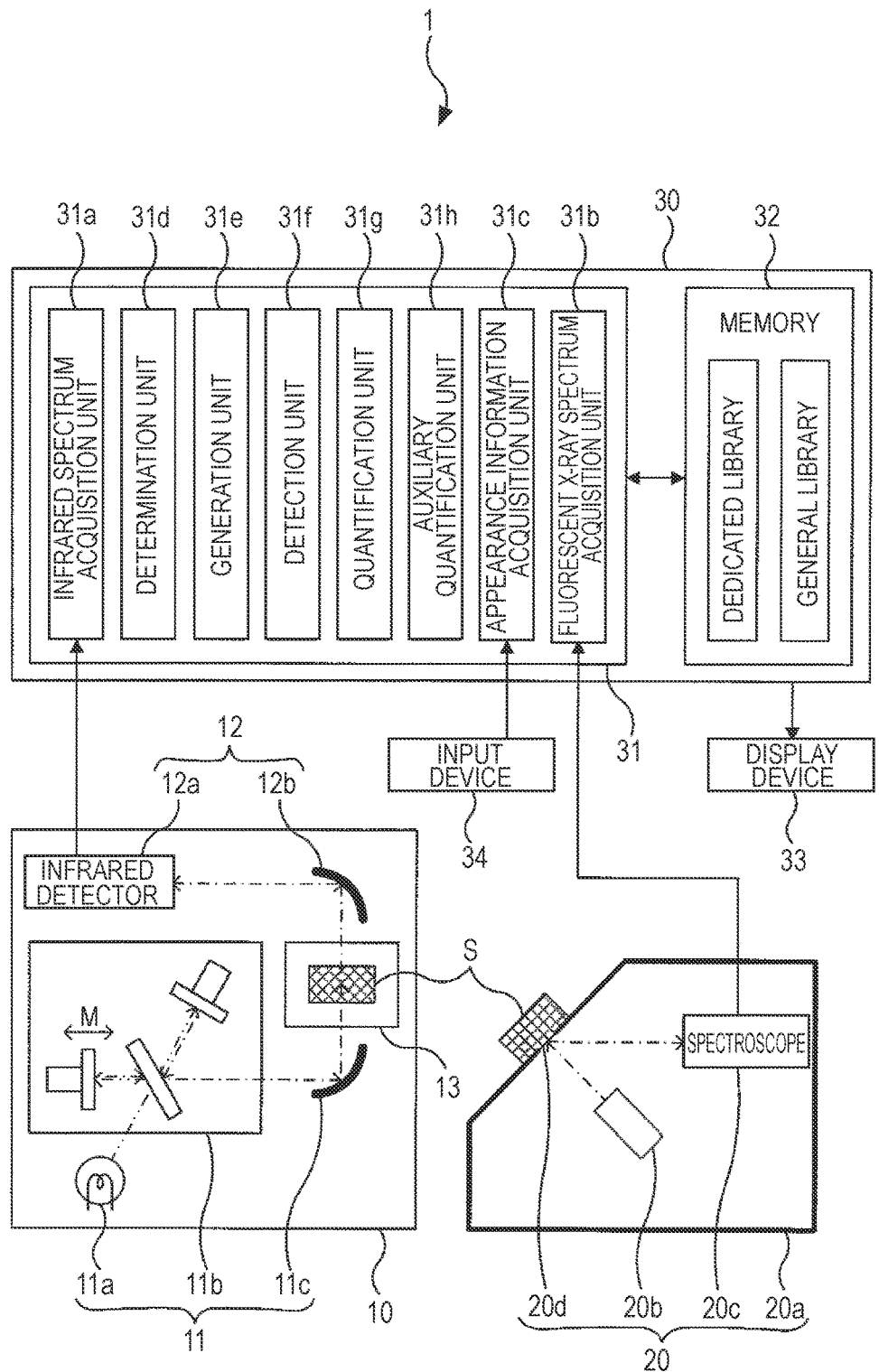
FIG. 1 is a configuration diagram illustrating a foreign substance analysis apparatus according to the invention.

FIG. 1 is a diagram illustrating a configuration of a foreign substance analysis apparatus according to the invention.

The foreign substance analysis apparatus (foreign substance analysis system) 1 is configured to include an FTIR 10, an EDX 20, and a computer 30.

The FTIR 10 is configured to include an infrared light source unit 11 that emits infrared light, an infrared light detection unit 12 having an infrared detector 12a that detects an interferogram (infrared light) and a mirror 12b, and a sample mount unit 13 on which a sample S is mounted.

The infrared light source unit 11 is configured to include an infrared light source 11a that emits the infrared light, a main interferometer main unit 11b that generates an interferogram, a mirror 11c, and the like. The infrared light emitted from the infrared light source 11a is irradiated on a beam splitter of the main interferometer main unit 11b.

In the main interferometer main unit 11b, a movable mirror unit having a movable mirror, a beam splitter, and a fixed mirror unit having a fixed mirror are arranged.

According to the main interferometer main unit 11b, the infrared light emitted from the infrared light source 11a is irradiated on the beam splitter and is divided in two directions of the movable mirror and the fixed mirror. The infrared light reflected by the movable mirror and the infrared light reflected by the fixed mirror return to the beam splitter, and these infrared lights are combined by the beam splitter to be transmitted to the mirror 11c. At this time, since the movable mirror reciprocally moves forward and backward in the incident optical axis direction M, a difference in the optical path lengths of the two divided light fluxes periodically changes, and the light directed from the beam splitter to the mirror 11c becomes an interferogram of which amplitude varies with time.

In the sample mount unit 13, when the sample S is mounted at a predetermined position (measurement position), a measurement point of the sample S is irradiated with the light collected by the mirror 11c, light reflecting or transmitting the measurement point of the sample S is condensed to the infrared detector 12a by the mirror 12b, and the infrared spectrum information obtained by the infrared detector 12a is output to the computer 30.

The EDX 20 is configured to include a spectroscope stand 20a, and a counter electrode 20b disposed upward and a spectroscope 20c into which emitted light is introduced are provided inside the spectroscope stand 20a. On the upper surface of the spectroscope stand 20a, an opening 20d is formed at a position facing the counter electrode 20b.

According to the EDX 20 as described above, the measurement point of the sample S is brought into contact with the opening 20d of the spectroscope stand 20a so as to close the opening 20d, discharging is performed between the measurement point and the counter electrode 20b, and the emitted light is introduced into the spectroscope 20c, so that spectrum having wavelength peculiar to each element is extracted and detected. Then, the fluorescent X-ray spectrum information obtained by the spectroscope 20c is output to the computer 30.

The computer 30 is configured to include a CPU (control unit) 31 and a memory 32 and is connected to the display device 33 and the input device 34.

In block forms, The functions processed by the CPU 31 include an infrared spectrum acquisition unit 31a that acquires the infrared spectrum information from the infrared detector 12a, a fluorescent X-ray spectrum acquisition unit 31b that acquires the fluorescent X-ray spectrum information from the spectroscope 20c, an appearance information acquisition unit 31c that acquires the appearance information from the input device 34, a determination unit 31d that determines whether or not an organic element is contained in the sample S, a generation unit (semi-quantification unit) 31e that generates the main component information on the basis of the fluorescent X-ray spectrum information, a detection unit 31f that detects N types of elements on the basis of the infrared spectrum information, the main component information, the appearance information and the dedicated library, a quantification unit 31g that qualitatively and quantitatively determining the elements contained in the sample S based on the fluorescent X-ray spectrum information, and an auxiliary quantification unit 31h that perform analysis on the basis of the infrared spectrum information, the main component information, and the general library.

In addition, the memory 32 stores a dedicated library and a general library in advance (storage step). The dedicated library indicates the relationship between appearance information (color, shape, hardness, and presence or absence of gloss) and element information in infrared spectrum information. In addition, the general library indicates the element information in the infrared spectrum information, and a commercially available product can be used as the general library.

The determination unit 31d compares the ratio of the intensity of the Compton scattered ray and the intensity of the Rayleigh scattered ray in the fluorescent X-ray spectrum information with "1.0 (set threshold value)" to perform control to determine whether or not an organic element is contained in the sample S. Specifically, when it is determined that the ratio is "1.0" or more, it is determined that the organic element is contained in the sample S. On the other hand, when it is determined that the ratio is less than "1.0", it is determined that the organic element is not contained in the sample S.

The generation unit (semi-quantification unit) 31e performs control to prepare main component information on the basis of the fluorescent X-ray spectrum information.

For example, in a case where the determination unit 31d determines that the organic element is contained in the sample S, the elements having contents of 0.1 wt% or more are detected by using $CH_2O$ balance. In a case where there are six or more types of elements, the elements having the first to fifth highest contents are detected, and these five types of elements are used for the main component information. In addition, in a case where any element having a content of 0.1 wt% or more cannot be detected, the elements having the first to third highest contents are detected, and these three types of elements are used or the main component information.

On the other hand, in a case where the determination unit 31d determines that no organic element is contained in the sample S, the elements having contents of 0.1 wt% or more are detected without using balance. In a case where there are six or more types of elements, the elements having the first to fifth highest contents are detected, and these five elements are used for the main component information. In addition, when an element having a content of 0.1 wt% or more cannot be detected, the elements having the first to third highest content are detected, and these three types of elements are used for the main component information.

The detection unit 31f performs control to detect N types of elements on the basis of the infrared spectrum information, the main component information, the appearance information, and the dedicated library.

For example, a search wavenumber range is limited for each element on the basis of the main component information, ten types of elements having high contents are detected by using the appearance information and the dedicated library and displayed on the display device 33. Furthermore, among these elements, the three types of elements having high contents are determined.

The quantification unit 31g performs control to qualitatively and quantitatively determining the elements contained in the sample S on the basis of the fluorescent X-ray spectrum information.

For example, the analyst checks the ten types of elements displayed by the detection unit 31f and inputs an input signal indicating whether the ten types of elements are used as the main components of the sample S or the three types of elements are used as the main components of the sample S by using the input device 34. As a result, on the basis of the input signal, the quantification unit 31g quantifies the elements contained in the sample S by using the three types of elements as the main components of the sample S or quantifies the elements contained in the sample S by using the ten types of the elements as the main components of the sample S.

The auxiliary quantification unit 31h performs control to detect M types of elements on the basis of the infrared spectrum information, the main component information, and the general library and control to finally quantify the elements contained in the sample S.

For example, when the analyst inputs an input signal indicating the desired number M of types of detection elements by the input device 34, the auxiliary quantification unit 31h detects the M types of elements on the basis of the received input signal, the infrared spectrum information, the main component information, and the general library and quantifies the elements contained in the sample S from the fluorescent X-ray spectrum information and the infrared spectrum information by using the M types of elements.

Figure 2:
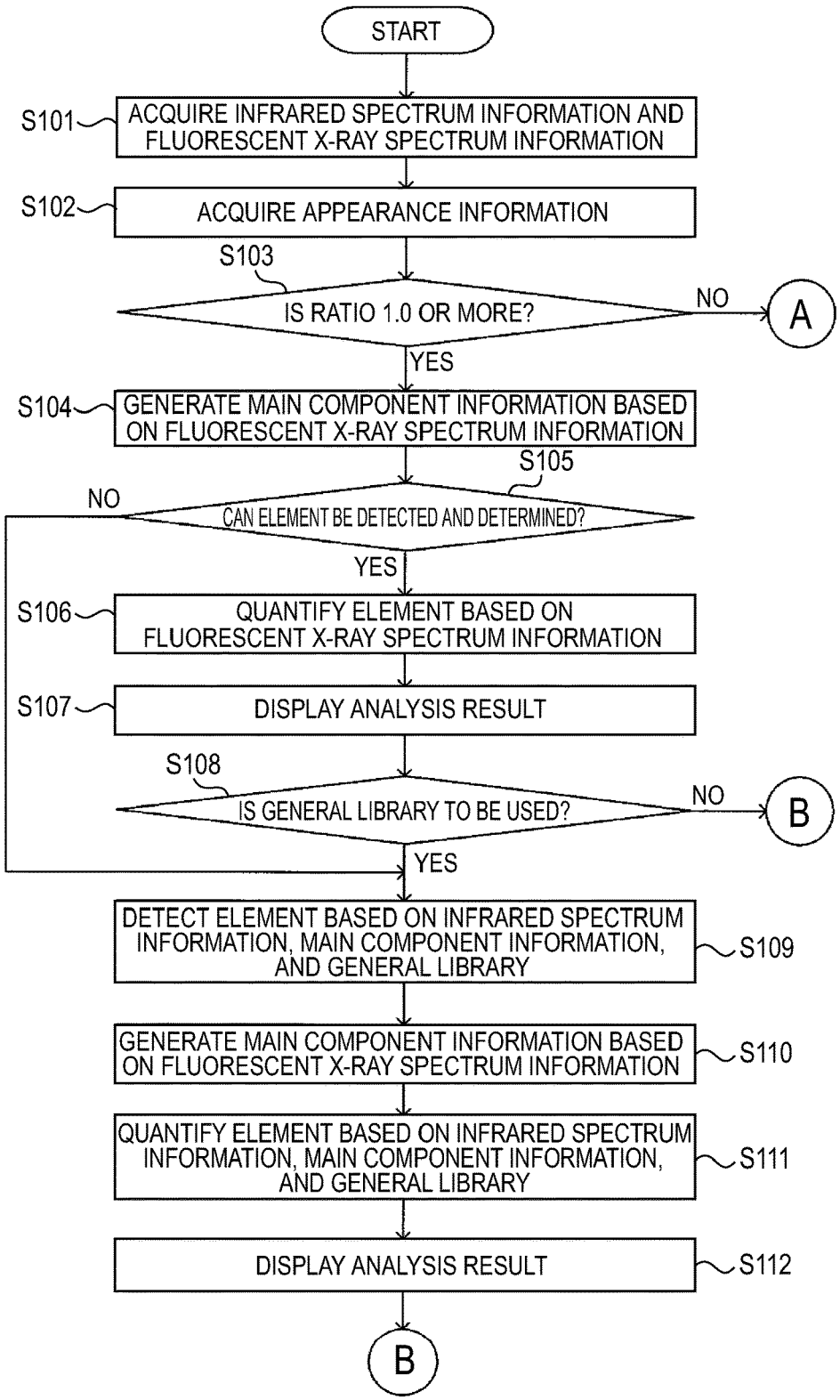
FIG. 2 is a flowchart illustrating a foreign substance analyzing method in the system according to the invention.
Figure 3:
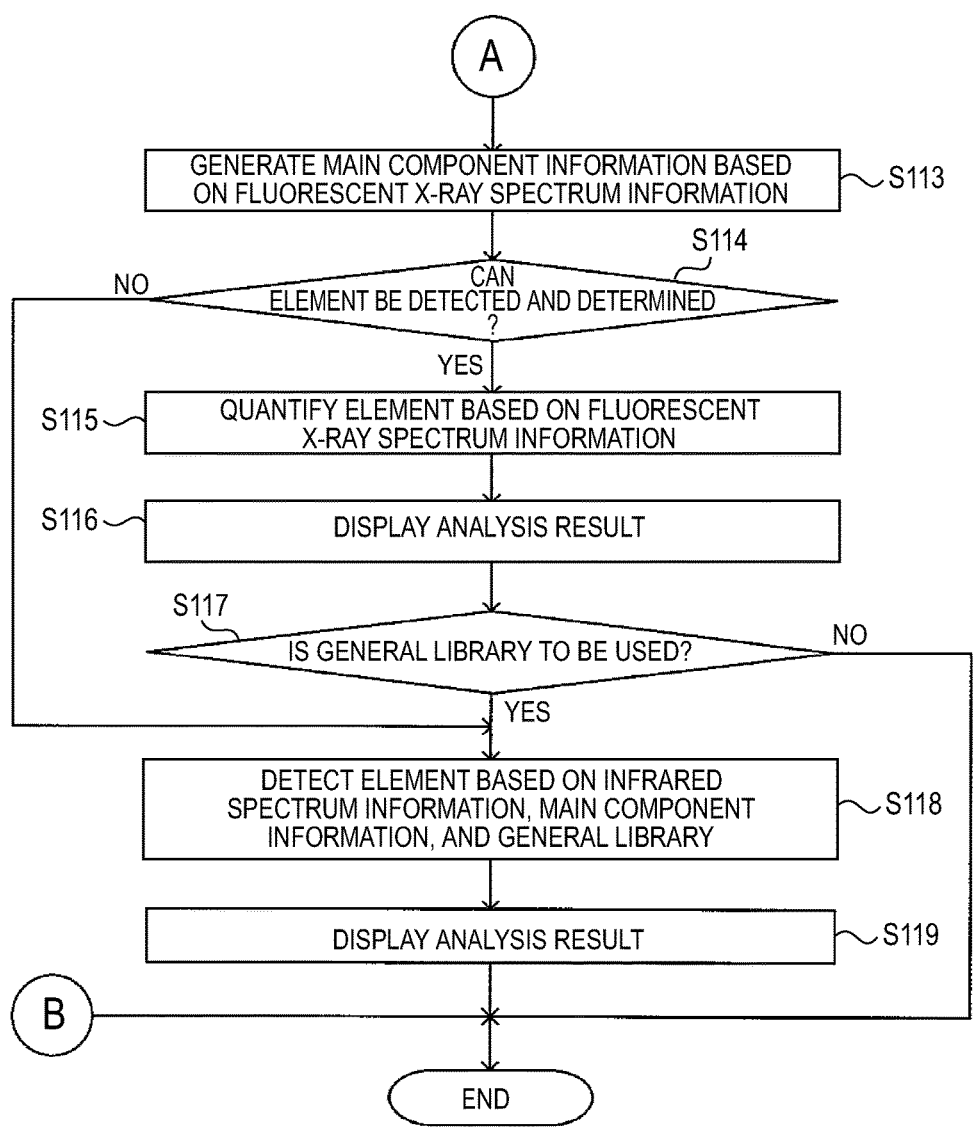
FIG. 3 is a flowchart illustrating a foreign substance analyzing method in the system according to the invention.

Herein, a foreign substance analyzing method (foreign substance analysis system) for analyzing the sample S with the foreign substance analysis apparatus 1 according to the invention will be described with reference to flowcharts of FIGS. 2 and 3.

First, in the process of step s101, the infrared spectrum acquisition unit 31a acquires the infrared spectrum information from the infrared detector 12a, and the fluorescent X-ray spectrum acquisition unit 31b acquires the fluorescent X-ray spectrum information from the spectroscope 20c.

Next, in the process of step s102, the appearance information acquisition unit 31c displays an input screen or the like on which the appearance information (color, shape, hardness, presence or absence of gloss) is input on the display device 33 and acquires the appearance information input by the analyst or the like.

Next, in the process of step s103, the determination unit 31d determines whether or not the ratio between the intensity of the Compton scattered ray and the intensity of the Rayleigh scattered ray in the fluorescent X-ray spectrum information is "1.0" or more. When it is determined that the ratio is "1.0" or more, in the process of step s104, the generation unit 31e generates main component information on the basis of the fluorescent X-ray spectrum information.

Next, in the process of step s105, the detection unit 31f detects ten types of elements having high contents on the basis of the infrared spectrum information, the main component information, and the dedicated library, displays the detected ten types of elements on the display device 33, and determines the three types of elements having high contents from the ten types of elements.

When the three types of elements having high contents can be determined in the process of step s105, in the process of step s106, the quantification unit 31g quantifies the elements contained in the sample S on the basis of the fluorescent X-ray spectrum information by using the ten types or three types of elements as the main components of the sample S.

Next, in the process of step s107, the infrared spectrum analysis result obtained in the process of step s105 and the fluorescent X-ray spectrum analysis result obtained in the process of step s106 are displayed on the display device 33.

Next, in the process of step s108, the analyst determines whether or not to perform analysis using the general library. When the use of the general library is selected or when the three types of elements having high content cannot be determined in the process of step s105 (when the three types of elements cannot be successfully hit), in the process of step s109, the auxiliary quantification unit 31h detects M types of elements on the basis of the infrared spectrum information, the main component information, and the general library.

Next, in the process of step s110, on the basis of the fluorescent X-ray spectrum information, by using M types of elements as the main components of the sample S, the auxiliary quantification unit 31h detects the elements of which contents are 0.1% by weight or more. When the number of types is 6 or more, the auxiliary quantification unit detects the elements having the first to fifth highest contents and uses these five types of elements for the main component information. In addition, when any element having a content of 0.1 wt% or more cannot be detected, the elements having the first to third highest contents are detected, and these three types of elements are used for the main component information.

Next, in the process of step s111, the auxiliary quantification unit 31h quantifies the elements contained in the sample S on the basis of the infrared spectrum information, the main component information, and the general library.

Next, in the process of step s112, the fluorescent X-ray spectrum analysis result obtained in the process of step s110 and the infrared spectrum analysis result obtained in the process of step s111 are displayed on the display device 33.

On the other hand, when it is determined in step s103 that the ratio is less than "1.0", in the processing of step s113, the generation unit 31e generates the main component information on the basis of the fluorescent X-ray spectrum information.

Next, in the process of step s114, the detection unit 31f detects ten types of elements having high contents on the basis of the infrared spectrum information, the main component information, and the dedicated library and displays the elements on the display device 33. Among these elements, the three types of elements having high contents are determined.

When the three types of elements having high contents can be determined in the process of step s114, in the process of step s115, the quantification unit 31g quantifies the elements contained in the sample S on the basis of the fluorescent X-ray spectrum information by using ten types or three types of elements as main components of the sample S.

Next, in the process of step s116, the infrared spectrum analysis result obtained in the process of step s114 and the fluorescent X-ray spectrum analysis result obtained in the process of step s115 are displayed on the display device 33.

Next, in the process of step s117, the analyst determines whether or not to perform analysis by using the general library. When the use of the general library is selected or when the three types of elements having high contents cannot be determined in the process of step s114, in the process of step s118, the auxiliary quantification unit 31h detects M types of elements on the basis of the infrared spectrum information, the main component information, and the general library.

Next, in the process of step s119, the fluorescent X-ray spectrum analysis result obtained in the process of step s113 and the infrared spectrum analysis result obtained in the process of step s117 are displayed on the display device 33.

Then, when it is determined that the general library is not used in the process of step s108 or the process of step s117, or when the process of step s112 or step s119 is completed, the flowchart is ended.

As described above, according to the foreign substance analysis system according to the invention, if infrared spectrum information and fluorescent X-ray spectrum information are acquired, the subsequent analysis is substantially automated, so that it is possible to realize a more-accurate mixed foreign substance analysis.

The invention can be appropriately used for a foreign substance analysis apparatus or the like capable of analyzing foreign substance contained in a sample.

What is claimed is:

1. A foreign substance analysis system comprising:
    an infrared spectrum acquisition step of acquiring infrared spectrum information of a sample measured by an infrared spectrophotometer,
    a fluorescent X-ray spectrum acquisition step of acquiring fluorescent X-ray spectrum information of the sample measured by a fluorescent X-ray analyzer;
    a determination step of determining whether or not an organic element is contained in the sample by comparing a ratio between an intensity of a Compton scattered ray and an intensity of a Rayleigh scattered ray in the fluorescent X-ray spectrum information with a set threshold value;
    an appearance information acquisition step of acquiring appearance information of the observed sample; and
    a storage step of storing a dedicated library indicating a relationship between the appearance information and element information in the infrared spectrum information.

2. The foreign substance analysis system according to claim 1, further comprising:
    a generation step of generating main component information indicating at least one type of element having a high content on the basis of the fluorescent X-ray spectrum information in assumption that a composition formula of main components of the sample is $CH_2O$ when it is determined that the organic element is included in the determination step;
    a detection step of detecting N types of elements having high contents on the basis of the infrared spectrum information, the main component information and a library; and
    a quantification step of using the N types of elements detected in the detection step as main components of the sample and quantifying the elements contained in the sample on the basis of the fluorescent X-ray spectrum information.

3. The foreign substance analysis system according to claim 1, further comprising:
    a generation step of generating main component information indicating at least one type of element having a high content on the basis of the fluorescent X-ray spectrum information when it is determined that the organic element is not contained in the determination step;
    a detection step of detecting N types of elements having high contents on the basis of the infrared spectrum information, the main component information, and the library; and
    a quantification step of using the N types of elements detected in the detection step as the main components of the sample and quantifying the element contained in the sample on the basis of the fluorescent X-ray spectrum information.

4. The foreign substance analysis system according to claim 1, wherein the appearance information is at least one of color, shape, hardness, and gloss.

5. The foreign substance analysis system according to claim 4,
    wherein, in the storage step, a general library indicating the element information in the infrared spectrum information is stored, and
    wherein, in the detection step, it is selected whether to use the dedicated library or to use the general library.

6. The foreign substance analysis system according to claim 1,
    wherein, in the storage step, a general library indicating the element information in the infrared spectrum information is stored, and
    wherein, in the detection step, it is selected whether to use the dedicated library or to use the general library.

* * * * *